United States Patent [19]
Washburn et al.

[11] Patent Number: 6,077,226
[45] Date of Patent: Jun. 20, 2000

[54] METHOD AND APPARATUS FOR POSITIONING REGION OF INTEREST IN IMAGE

[75] Inventors: Michael Joseph Washburn, New Berlin; Patrick R. Meyers, Mequon, both of Wis.

[73] Assignee: General Electric Company, Milwaukee, Wis.

[21] Appl. No.: 09/281,192

[22] Filed: Mar. 30, 1999

[51] Int. Cl.[7] .................................................. A61B 8/00
[52] U.S. Cl. ............................................ 600/443; 600/447
[58] Field of Search .................................. 600/437, 440, 600/443, 447, 454; 348/169, 699; 382/107, 207, 236; 128/916

[56] References Cited

U.S. PATENT DOCUMENTS

| | | | |
|---|---|---|---|
| 5,538,004 | 7/1996 | Bamber | 600/443 |
| 5,953,439 | 9/1999 | Ishihara et al. | 382/107 |
| 5,976,088 | 11/1999 | Urbano et al. | 600/443 |
| 6,017,309 | 1/2000 | Washburn et al. | 600/454 |

*Primary Examiner*—Marvin M. Lateef
*Assistant Examiner*—Ali M. Imam
*Attorney, Agent, or Firm*—Dennis M. Flaherty; Christian G. Cabou; Phyllis Y. Price

[57] ABSTRACT

A method and apparatus for adjusting the shape of a region of interest (ROI) in a frame of imaging data in response to an operator-actuated change in the depth of the ROI. The displayed image has a background region of data acquired using a first imaging mode and an ROI of data acquired using a second imaging mode. The ROI is surrounded by the background region and bounded by an ROI graphic. The adjustment in the shape of the ROI is accomplished by programming the imaging system with an algorithm that maintains the height and the bottom width of the ROI substantially constant. Only the top width of the ROI and the angles of the edge lines are automatically changed in response to the operator-actuated change in ROI depth.

32 Claims, 7 Drawing Sheets

METHOD AND APPARATUS FOR POSITIONING REGION OF INTEREST IN IMAGE

FIELD OF THE INVENTION

This invention generally relates to imaging in which a region of interest is superimposed on a background image frame. In particular, the invention relates to methods and apparatus for adjusting a region of interest relative to a sector-shaped background image frame in ultrasound imaging of biological tissues.

BACKGROUND OF THE INVENTION

Conventional ultrasound scanners create two-dimensional B-mode images of tissue in which the brightness of a pixel is based on the intensity of the echo return. Alternatively, in a color Doppler mode, the movement of fluid (e.g., blood) or tissue can be imaged. Measurement of blood flow in the heart and vessels using the Doppler effect is well known. The phase shift of backscattered ultrasound waves may be used to measure the velocity of the backscatterers from tissue or blood. The Doppler shift may be displayed using different colors to represent speed and direction of flow. Alternatively, in power Doppler imaging, the power contained in the returned Doppler signal is displayed.

Conventional ultrasound imaging systems comprise an array of ultrasonic transducer elements arranged in one or more rows and driven with separate voltages. By selecting the time delay (or phase) and amplitude of the applied voltages, the individual transducer elements in a given row can be controlled to produce ultrasonic waves which combine to form a net ultrasonic wave that travels along a preferred vector direction and is focused at a selected point along the beam. The beamforming parameters of each of the firings may be varied to provide a change in maximum focus or otherwise change the content of the received data for each firing, e.g., by transmitting successive beams along the same scan line with the focal point of each beam being shifted relative to the focal point of the previous beam. In the case of a steered array, by changing the time delays and amplitudes of the applied voltages, the beam with its focal point can be moved in a plane to scan the object. In the case of a linear array, a focused beam directed normal to the array is scanned across the object by translating the aperture across the array from one firing to the next.

The same principles apply when the transducer probe is employed to receive the reflected sound in a receive mode. The voltages produced at the receiving transducer elements are summed so that the net signal is indicative of the ultrasound reflected from a single focal point in the object. As with the transmission mode, this focused reception of the ultrasonic energy is achieved by imparting separate time delay (and/or phase shifts) and gains to the signal from each receiving transducer element.

A single scan line (or small localized group of scan lines) is acquired by transmitting focused ultrasound energy at a point, and then receiving the reflected energy over time. The focused transmit energy is referred to as a transmit beam. During the time after transmit, one or more receive beamformers coherently sum the energy received by each channel, with dynamically changing phase rotation or delays, to produce peak sensitivity along the desired scan lines at ranges proportional to the elapsed time. The resulting focused sensitivity pattern is referred to as a receive beam. A scan line's resolution is a result of the directivity of the associated transmit and receive beam pair.

A B-mode ultrasound image is composed of multiple image scan lines. The brightness of a pixel is based on the intensity of the echo return from the biological tissue being scanned. The outputs of the receive beamformer channels are coherently summed to form a respective pixel intensity value for each sample volume in the object region or volume of interest. These pixel intensity values are log-compressed, scan-converted and then displayed as a B-mode image of the anatomy being scanned.

In addition, ultrasonic scanners for detecting blood flow based on the Doppler effect are well known. Such systems operate by actuating an ultrasonic transducer array to transmit ultrasonic waves into the object and receiving ultrasonic echoes backscattered from the object. In the measurement of blood flow characteristics, returning ultrasonic waves are compared to a frequency reference to determine the frequency shift imparted to the returning waves by flowing scatterers such as blood cells. This frequency, i.e., phase, shift translates into the velocity of the blood flow. The blood velocity is calculated by measuring the phase shift from firing to firing at a specific range gate.

The change or shift in backscattered frequency increases when blood flows toward the transducer and decreases when blood flows away from the transducer. Color flow images are produced by superimposing a color image of the velocity of moving material, such as blood, over a black and white anatomical B-mode image. Typically, color flow mode displays hundreds of adjacent sample volumes simultaneously laid over a B-mode image, each sample volume being color-coded to represent velocity of the moving material inside that sample volume at the time of interrogation.

Ultrasound scanners which perform color Doppler imaging employ an ROI which specifies the area of the gray-scale B-mode image to overlay with color Doppler data. The ROI is often made smaller than the B-mode image in order to maintain an acceptable acoustic frame rate. The scanner is programmed to allow the operator to move the ROI about the B-mode image area. In the case where a straight linear transducer is used, both the B-mode image area and the ROI are rectangles. Thus, as the depth of the ROI is changed, there is no need to automatically change the height or width of the ROI. However, in the cases where either a curved linear or a sector transducer is used, the scanner is programmed to automatically adjust the ROI size as the operator moves the ROI about the B-mode image area. In accordance with the conventional algorithm, the ROI is typically placed on or near the center of the B-mode image area. If the operator moves the ROI deeper in the image, the height of the ROI remains unchanged and the width of the ROI is changed automatically to accommodate the same number of vectors that were contained in the ROI at its previous position. Since the vectors are diverging with depth, the ROI width is increased as its depth increases. If instead the operator moves the ROI shallower in the image, the same algorithm is used, which results in a narrower ROI. Following the change in ROI position initiated by the operator and the automatic change in ROI width in response to that position change, the operator may then adjust the ROI width to restore the original ROI width. This latter adjustment is desirable in the case where the depth of the ROI is increased because the resulting acoustic frame rate will be increased. This conventional method of operating an ultrasound scanner has the disadvantage that an additional adjustment must be made by the operator following increase in ROI depth in order to gain the benefit of increased acoustic frame rate.

SUMMARY OF THE INVENTION

In accordance with one aspect of the invention, a displayed image comprises a background region of data acquired using a first imaging mode and an ROI of data acquired using a second imaging mode different than the first imaging mode, the ROI being surrounded by the background region and bounded by an ROI graphic. As the position of the displayed ROI graphic is changed in depth by the system operator, the configuration of the ROI graphic is automatically adjusted in a manner that maintains the width of the ROI better than the conventional method. As a result, the operator is less likely to need to modify the width of the ROI after a change in the depth of the ROI, and when the operator moves the ROI deeper into the image, fewer vectors are used and a higher acoustic frame rate is achieved. The invention has application in ultrasound imaging and other imaging modalities.

The preferred embodiments involve ultrasound imaging. In accordance with one preferred embodiment, the first imaging mode is the B mode and the second imaging mode is the color Doppler mode. In another preferred embodiment, the first imaging mode is the B mode and the second imaging mode is a zoom B mode. In yet another preferred embodiment, the first imaging mode is a non-optimal image quality B mode and the second imaging mode is an optimal image quality B mode.

The adjustment in the shape of the ROI in response to change in depth is accomplished by programming the ultrasound scanner with an algorithm that maintains the height and the bottom width of the ROI substantially constant. Only the top width of the ROI and the angles of the edge lines are automatically changed in response to the operator-actuated change in ROI depth.

Initially, the ROI is typically placed on or near the center of the B-mode image area. In accordance with the preferred embodiment of the algorithm, if the user moves the ROI deeper in the image, the height and bottom width of the ROI are not changed. The width at the top of the ROI is increased and the angles of the edge lines of the ROI are changed such that the ROI edge lines are parallel to the leftmost and rightmost vectors respectively within the bottom of the ROI. If instead, the user moves the ROI shallower in the image, the height and bottom width of the ROI are again unchanged. The width at the top of the ROI is decreased and the angles of the edge lines of the ROI are again changed such that the ROI edge lines are parallel to the leftmost and rightmost vectors respectively within the bottom of the ROI. This algorithm results in an ROI which maintains its width better than the conventional method.

DETAILED DESCRIPTION OF THE PREFERRED EMBODIMENTS

Figure 1:
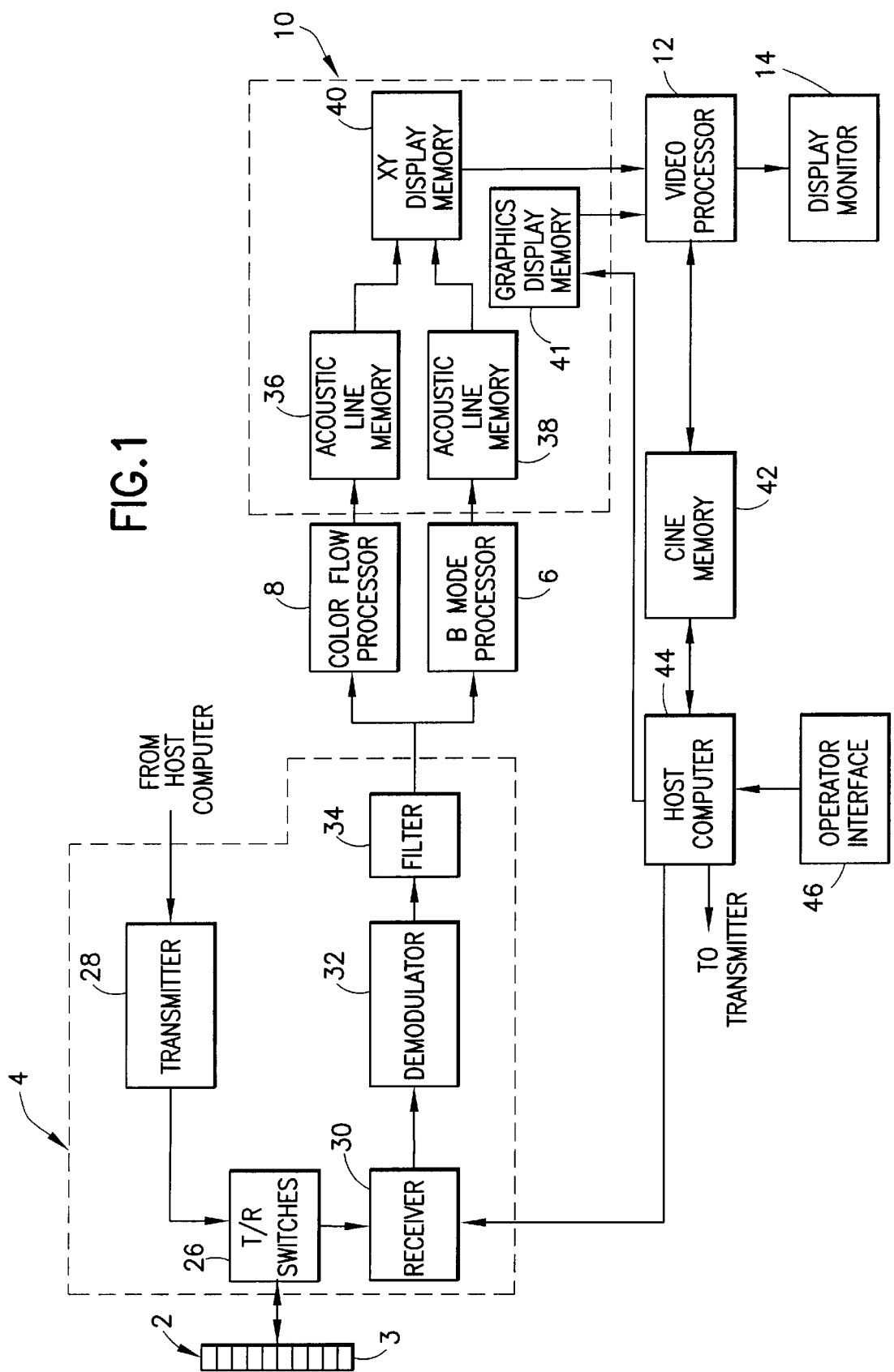
FIG. 1 is a block diagram showing the B mode and color flow mode signal processing chains for one type of ultrasound imaging system in which the present invention can be incorporated.

Referring to FIG. 1, the ultrasound imaging system comprises a transducer array 2 consisting of a plurality of separately driven transducer elements 3. The transducer is connected to a beamformer 4 comprising a transmitter 28 and a receiver 30. In a transmit mode, a set of transmit/receive (T/R) switches 26 couple the transducer elements to transmitter 28. Each transducer element 3 produces a burst of ultrasonic energy when energized by a respective pulsed waveform produced by transmitter 28. In a receive mode, the T/R switches 26 couple the transducer elements to receiver 30. The ultrasonic energy reflected back to transducer array 2 from the object under study is converted to an analog electrical signal by each receiving transducer element 3 and applied separately to receiver 30. The transmitter and receiver are operated under control of a host computer (i.e., master controller) 44. A complete scan is performed by acquiring a series of echoes in which transmitter 28 is gated ON momentarily to energize each transducer element 3 in the transmit aperture, and the subsequent echo signals produced by each transducer element are applied to receiver 30. The receiver 30 converts the analog echo signals to digital signals and combines the respective digital signals derived from each transducer element to produce a single beam-summed signal which is used to produce a line in an image displayed by a display monitor 14.

Figure 3:
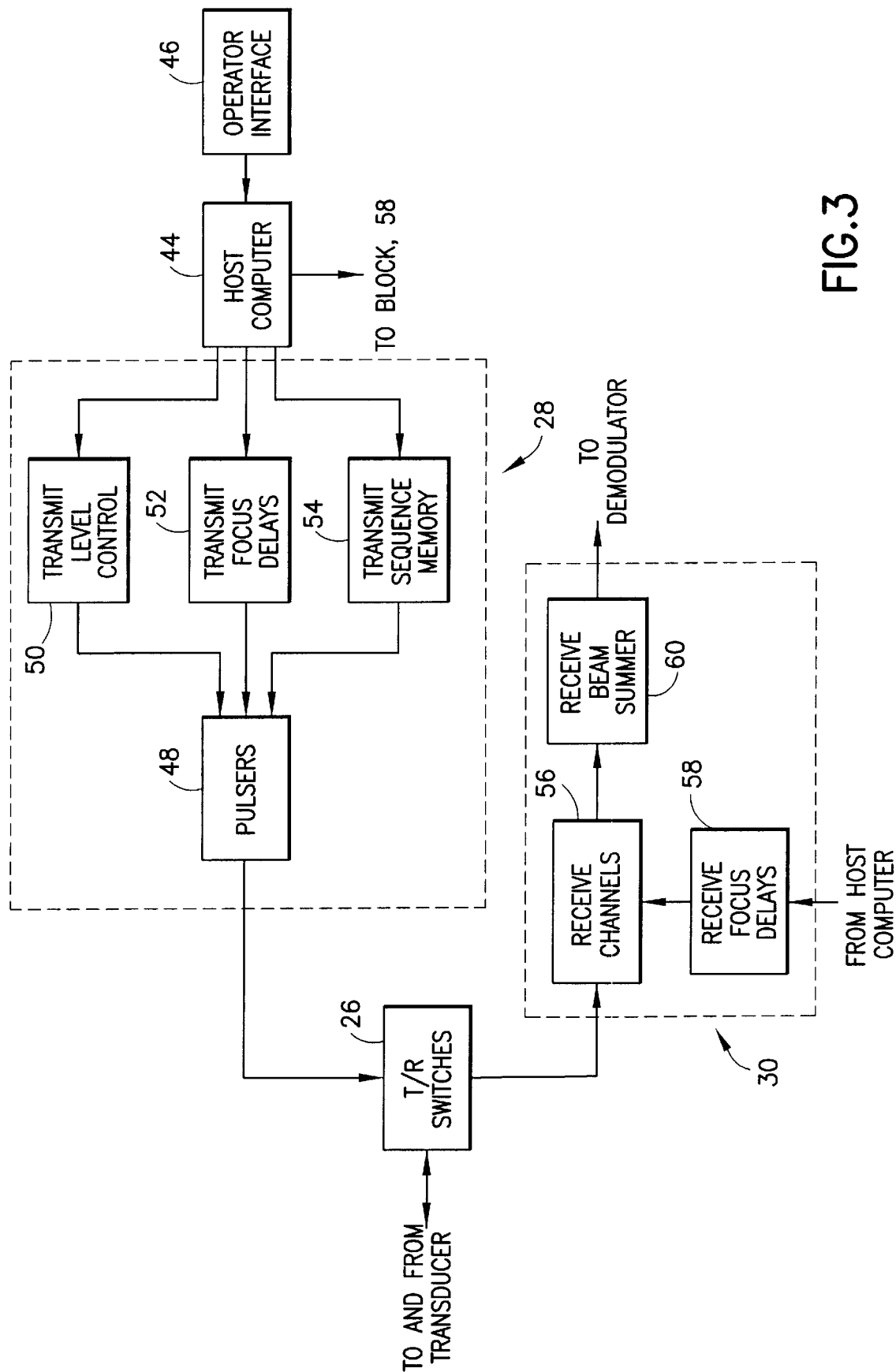
FIG. 3 is a block diagram showing the transmitter and receiver of FIG. 2 in greater detail.

Referring to FIG. 3, each transducer element in a transmit aperture is pulsed by a pulse waveform output by a respective pulser 48 in response to a respective transmit sequence output to that pulser from a transmit sequence memory 54. Adjustment of the transmit waveform frequency and/or length is implemented by programming transmit sequence memory 54. The frequency and length of each pulse waveform is determined by the respective transmit sequence. For example, if the pulsers 48 are bipolar, +1 and −1 elements of a transmit sequence are transformed into pulses of opposite phase by each pulser, while 0 elements correspond to no pulse. The duty cycle or pulse width is proportional to the number of consecutive +1's or −1's in the transmit sequence.

Under the direction of the host computer 44, the transmitter 28 drives the transducer array 2 such that the ultrasonic energy is transmitted as a directed focused beam. To accomplish focusing, respective time delays are imparted to the pulsers 48 by a transmit focus delay block 52, while respective pulse amplitudes are set by transmit level control block 50. The pulsers send the transmit pulses to elements of the transducer array 2 via the T/R switches 26. By appropriately adjusting the transmit focus time delays in a conventional manner, an ultrasonic beam can be directed and focused at a transmit focal zone position. The axial length of the transmit focal zone is a function of the width of the transmit aperture.

The host computer 44 determines the conditions under which the acoustic pulses will be transmitted. With this information, the transmit focus delay and transmit level control blocks will respectively determine the timing and the amplitude of each of the transmit pulses to be generated by the pulsers 48, while the frequency and length of the transmit pulses are determined by the transmit sequences. The host computer can provide different sets of transmit sequences, transmit focus delays and transmit levels for B-mode and color flow mode imaging.

After each transmit, the T/R switches 26 are switched to receive mode to accept the returning echoes backscattered from the object being scanned. These return signals are fed to respective receive channels 56 of the receiver 30. Each receive channels includes an analog-to-digital converter. The receiver tracks echoes under the direction of the host computer 44 by imparting the proper receive focus time delays 58 to the received RF echo signals. The beam summer 60 sums the RF echo signals for each firing to provide an echo signal which accurately indicates the total ultrasonic energy reflected from a succession of ranges corresponding to the particular transmit focal position.

Referring again to FIG. 1, in baseband imaging systems the beamsummed signal is output to a demodulator 32, which converts the beamsummed signal into baseband in-phase I and quadrature Q data vectors. The I and Q acoustic data vectors from the demodulator 32 are output to an FIR filter 34, which is provided with filter coefficients from a filter coefficient memory (not shown). The filter coefficient memory is programmed by the host computer 44.

The acoustic data from filter 34 is sent to a switch (not shown). In the B mode, acoustic data vectors acquired during scanning of an entire image frame are output to the B-mode processor 6. In the color flow mode, acoustic data vectors acquired during scanning of an ROI are output to a color flow processor 8. Depending on whether the acoustic data is for the background image or the ROI, the output of filter 34 is channeled to the appropriate processor.

Figure 2:
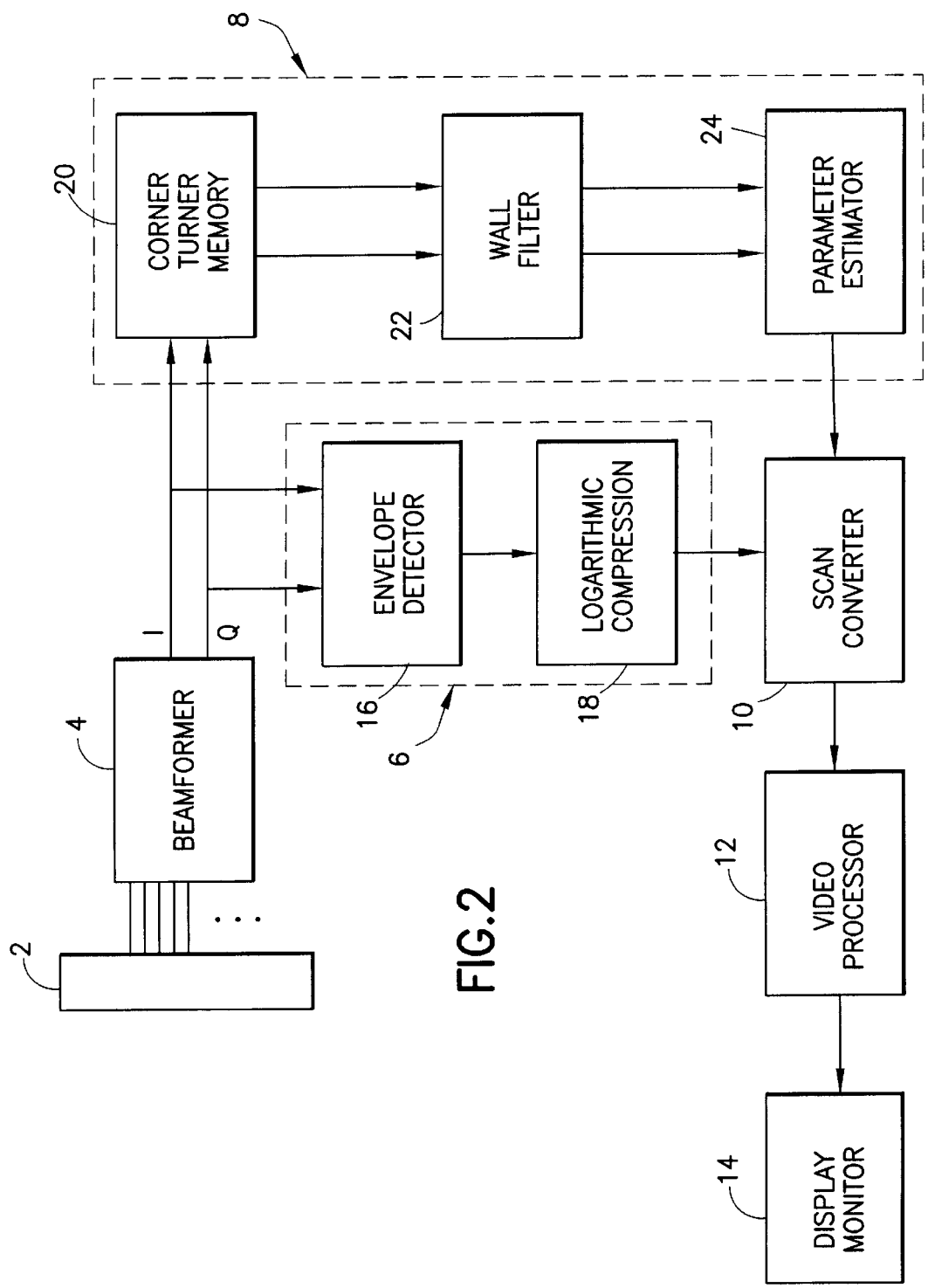
FIG. 2 is a block diagram showing additional components of the system depicted in FIG. 1.

In the B mode, the B-mode processor 6 detects the envelope of the streams of I and Q acoustic data (envelope detector 16 in FIG. 2) and then log-compresses the respective signal envelopes (logarithmic compression block 18 in FIG. 2). The envelope of a baseband signal is the magnitude of the vector which I and Q represent. The I,Q phase angle is not used in the B-mode display. The magnitude (i.e., intensity) of the signal is the square root of the sum of the squares of the orthogonal components, i.e., $(I^2 + Q^2)^{1/2}$.

Referring again to FIG. 1, the B-mode intensity data is output to a B-mode acoustic line memory 38 in the scan converter 10. The acoustic line memory 38 accepts the processed vectors of B-mode intensity data acquired during scanning of the background area and interpolates where necessary. The acoustic line memory 38 also performs the coordinate transformation of the B-mode intensity data from polar coordinate (R—θ) sector format or Cartesian coordinate linear format to appropriately scaled Cartesian coordinate display pixel intensity data. The pixel intensity data for background image area is written into an X-Y display memory 40.

The scan-converted B-mode image frame stored in the X-Y display memory 40 is passed to a video processor 12, which converts the pixel intensity data to the video frame rate and then maps the pixel intensity data to a gray-scale mapping for video display. A conventional ultrasound imaging system typically employs a variety of gray maps, which are simple transfer functions of the raw intensity data to display gray-scale levels. The gray-scale image frames are then sent to the display monitor 14 for display.

Before gray mapping, successive frames of display pixel intensity data in the video processor 12 are stored in a cine memory 42 on a first-in, first-out basis. Storage can be continuous or as a result of an external trigger event. The cine memory 42 is like a circular image buffer that runs in the background, capturing image data that is displayed in real time to the user. When the user freezes the system (by operation of an appropriate device on the operator interface 46), the user has the capability to view image data previously captured in cine memory.

System control is centered in host computer 44, which accepts operator inputs through the operator interface 46 (e.g., a control panel) and in turn controls the various subsystems. The host computer 44 performs system level control functions. A system control bus (not shown) provides the interface from the host computer to the subsystems. The host computer preferably incorporates a scan controller (not shown) which provides real-time (acoustic vector rate) control inputs to the various subsystems. The scan controller is programmed by the host computer CPU with the vector sequences and synchronization options for acoustic frame acquisitions. Thus, the scan controller controls the beam distribution and the beam density. The scan controller transmits the beam parameters defined by the host computer CPU to the subsystems via a scan control bus (not shown). Alternatively, the scan controller can be a separate dedicated processor programmed by the host computer.

The B-mode images displayed by monitor 14 are produced from an image frame of data in which each datum indicates the intensity or brightness of a respective pixel in the display. An image frame may, e.g., comprise a 256 × 256 data array in which each display pixel intensity datum is an 8-bit binary number that indicates pixel brightness. Each pixel has an intensity value which is a function of the backscatter cross section of a respective sample volume in response to interrogating ultrasonic pulses and the gray map employed. The displayed image represents the tissue and/or blood flow in a scan plane through the body being imaged.

In the color flow mode, the color flow processor 8 converts the streams of I and Q acoustic data into color flow estimates of velocity or power. Given the angle θ between the insonifying beam and the flow axis, the magnitude of the velocity vector can be determined by the standard Doppler equation:

$$v = cf_d/(2f_0 \cos \theta) \tag{1}$$

where c is the speed of sound in blood, $f_0$ is the transmit frequency and $f_d$ is the motion-induced Doppler frequency shift in the backscattered ultrasound.

In one conventional ultrasound imaging system, the ultrasound transducer array 2 is activated to transmit a series of multi-cycle (typically 4–8 cycles) waveforms which are focused at the same transmit focal position with the same transmit characteristics. These waveforms are fired at a pulse repetition frequency (PRF). A series of transmit firings focused at the same transmit focal position are referred to as a "packet". Each transmit beam propagates through the object being scanned and is reflected by ultrasound scatterers such as blood cells. The return signals are detected by the elements of the transducer array and then formed into a receive beam by receiver 30. This process is repeated for multiple points in an ROI selected by the system operator via an operator interface 46.

The traditional color firing sequence is a series of firings focused at the same transmit focal position, which firings produce the respective receive signals:

$$F_1 \; F_2 \; F_3 \; F_4 \ldots F_M \tag{1}$$

where $F_i$ is the receive signal for the i-th firing and M is the number of firings in a packet. These receive signals are then sent to the color flow processor 8. Referring to FIG. 2, a typical color flow processor 8 comprises a corner turner memory 20, respective wall filters 22 for the I/Q components, and a parameter estimator 24. The I/Q components are loaded into the corner turner memory 20, whose purpose is to buffer data from possibly interleaved firings and output the data as vectors of points across firings at a given range cell. Data is received in "fast time", or sequentially down range (along a vector) for each firing. The resultant "slow time" I/Q signal samples are passed through respective wall filters 22. In a typical system, each wall filter is a high pass filter which is applied to each down range position across firings, i.e., in "slow time". In the simplest case of a (1, −1) wall filter, each range point will be filtered to produce the respective difference signals:

$$(F_1 - F_2) \; (F_2 - F_3) \; (F_3 - F_4) \ldots (F_{M-1} - F_M)$$

and these differences are input to the color flow parameter estimator 24.

The purpose of the wall filter is to remove signal components produced by tissue surrounding the blood flow of interest. If these signal components are not removed, the resulting velocity estimate will be a combination of the velocities from the blood flow and the surrounding tissue. The backscatter component from tissue is many times larger than that from blood, so the velocity estimate will most likely be more representative of the tissue, rather than the blood flow. In order to get the flow velocity, the tissue signal must be filtered out.

The wall-filtered outputs are fed into the parameter estimator 24, which converts the range cell information into the intermediate autocorrelation parameters N, D, and R(0). N and D are the numerator and denominator for the autocorrelation equation, as shown below:

$$N = \sum_{i=1}^{M-1} (I_i Q_{i+1} - I_{i+1} Q_i) \tag{2}$$

$$D = \sum_{i=1}^{M-1} (I_i I_{i+1} + Q_i Q_{i+1}) \tag{3}$$

where $I_i$ and $Q_i$ are the input data for firing i, and M is the number of firings in the packet. R(0) is approximated as a finite sum over the number of firings in a packet, as follows:

$$R(0) = \sum_{i=1}^{M-1} \frac{(I_i^2 + Q_i^2 + I_{i+1}^2 + Q_{i+1}^2)}{2} \tag{4}$$

R(0) indicates the power in the returned ultrasound echoes.

A processor in parameter estimator 24 converts N and D into a magnitude and phase for each range cell. The equations used are as follows:

$$|R(T)| = \sqrt{N^2 + D^2} \tag{5}$$

$$\phi(R(T)) = \tan^{-1}\left[\frac{N}{D}\right] \tag{6}$$

The parameter estimator 24 processes the magnitude and phase values into estimates of power, velocity and turbulence. The phase is used to calculate the mean Doppler frequency, which is proportional to the velocity as shown below; R(0) and |R(T)| (magnitude) are used to estimate the turbulence.

The mean Doppler frequency is obtained from the phase of N and D and the pulse repetition time T:

$$\bar{f} = \frac{1}{2\pi T} \tan^{-1}\left[\frac{N}{D}\right] = \frac{1}{2\pi T}(\phi(R(T))) \tag{7}$$

The mean velocity is calculated using the Doppler shift equation:

$$\bar{v} = \frac{\bar{f}}{f_0} \frac{c}{2\cos\theta} \tag{8}$$

The parameter estimator 24 does not calculate the mean Doppler frequency as an intermediate output, but calculates $\bar{v}$ directly from the phase output of a processor using a lookup table. Typically the power estimates are compressed before scan conversion, e.g., using logarithmic compression (not shown).

The color flow estimates (i.e., power or velocity) are sent to a color flow acoustic line memory 36 of scan converter 10, which converts the color images into X-Y format for video display and stores the converted image in the X-Y display memory 40. The scan-converted color images are then passed to the video processor 12, which maps the video data to a display color map for video display. The color flow image data is then sent to the video monitor 14 for display in an ROI superimposed on the B-mode image data.

Figure 4:
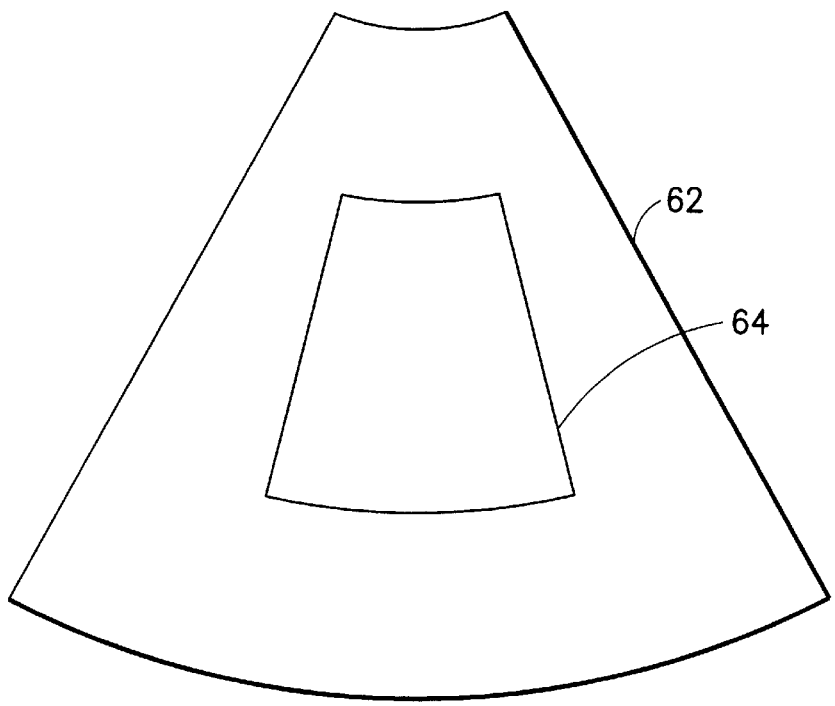
FIG. 4 is a schematic depicting a sector scan in which an ROI image is superimposed on a background image area at a default position in accordance with a conventional technique.

Referring to FIG. 4, during display an ROI graphic 64 is superimposed on the B-mode image area 62. Within the perimeter of that ROI graphic, color flow data is superimposed on the B-mode data. FIG. 4 shows the default position for the ROI graphic. The display data representing the ROI graphic 64 in the default position is generated by the host computer 44 and stored in a graphics display memory 41 of the scan converter 10. Alternatively, the graphics data can be generated by a dedicated graphics processor which communicates with the host computer. The ROI graphic data is output from graphics display memory 41 to the video processor 12 for continuous display, i.e., as the color flow and B-mode data for each successive image frame are displayed, an unchanging ROI is displayed to demarcate the boundary of the color flow data superimposed on the B-mode data.

In accordance with the preferred embodiment of the present invention, the width and height of the ROI can be adjusted by manipulation of respective control knobs on the operator interface 46. The position of the ROI can be changed by manipulation of a third control knob. Alternatively, the position and size of the ROI can be adjusted via any other standard user interface device (e.g., a trackball).

Depending on the dimensions and position of the ROI, in the color flow mode the host computer 44 will provide the required beam parameters to the transmitter 28 and to the receiver 30. The ROI imaging parameters, including transmit waveforms, number of transmit focal zones, vector spacing, filter coefficients and frame rates, are all independent of those for the background B-mode image.

Figure 5:
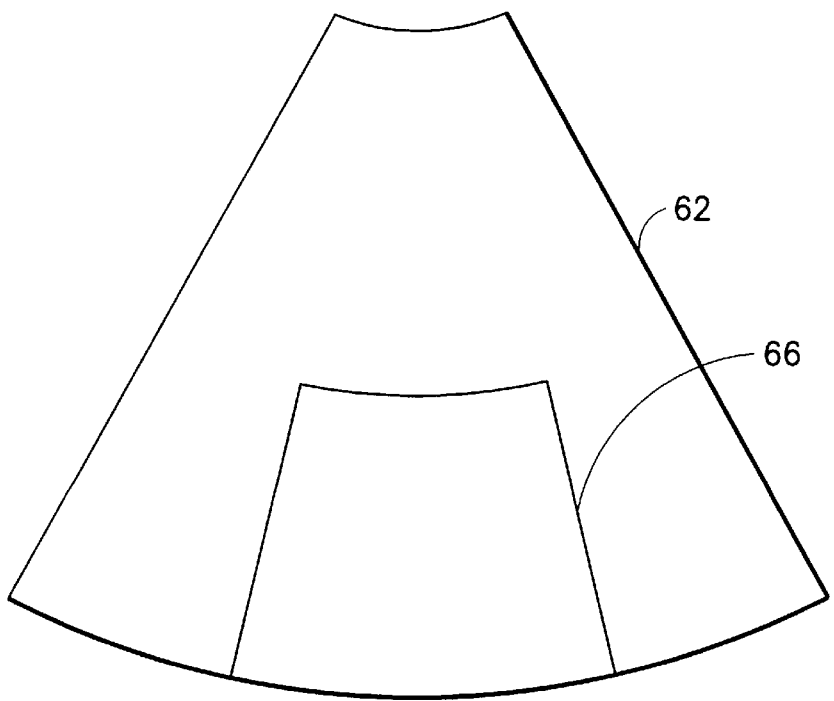
FIG. 5 is a schematic depicting a sector scan in which the ROI image of FIG. 4 has been moved to the bottom of the background image area and adjusted in accordance with a conventional algorithm.
Figure 6:
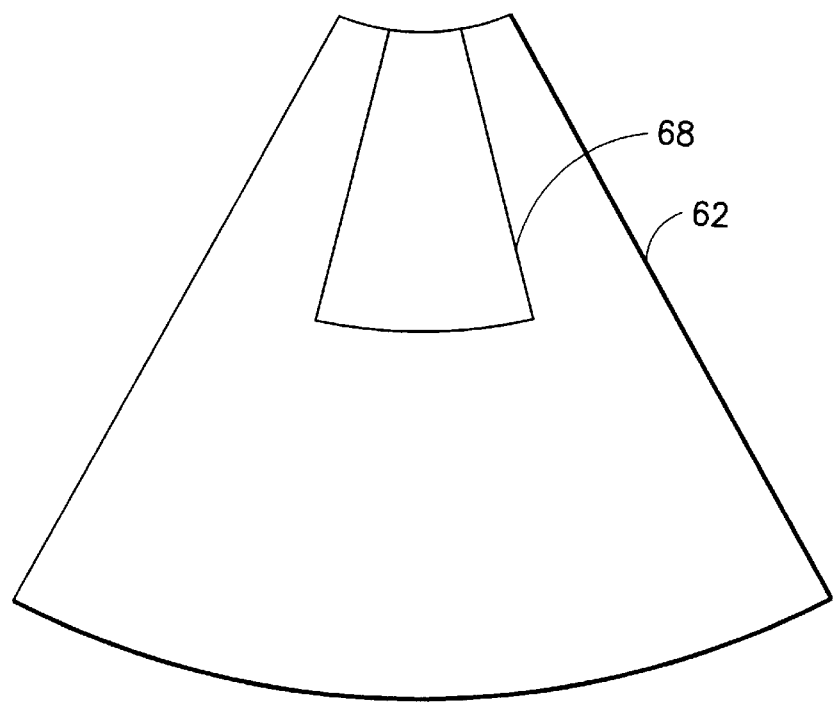
FIG. 6 is a schematic depicting a sector scan in which the ROI image of FIG. 4 has been moved to the top of the background image area and adjusted in accordance with the conventional algorithm.

In a conventional system, the default position of the ROI 64 is typically on or near the center of the B-mode image area 62, as depicted in FIG. 4. In accordance with a known algorithm, as the ROI is moved by the operator, the system automatically reconfigures the ROI to maintain a constant number of vectors therein. If the operator moves the ROI deeper in the image, the height of the ROI remains unchanged and the width of the ROI is changed automatically to accommodate the same number of vectors that were contained in the ROI at its previous position, thereby maintaining the acoustic frame rate constant. Such a deeper ROI is designated by numeral 66 in FIG. 5. Since the vectors are diverging with depth, the width of ROI 66 in FIG. 5 is greater than the width of the ROI 64 in FIG. 4. If the operator moves the ROI shallower in the image, the same algorithm produces a narrower ROI. Such a narrower ROI is designated by numeral 68 in FIG. 6. Following a change in ROI position initiated by the operator and the automatic change in ROI width in response to that position change, the operator may then adjust the ROI width to restore the original ROI width.

Figure 7:
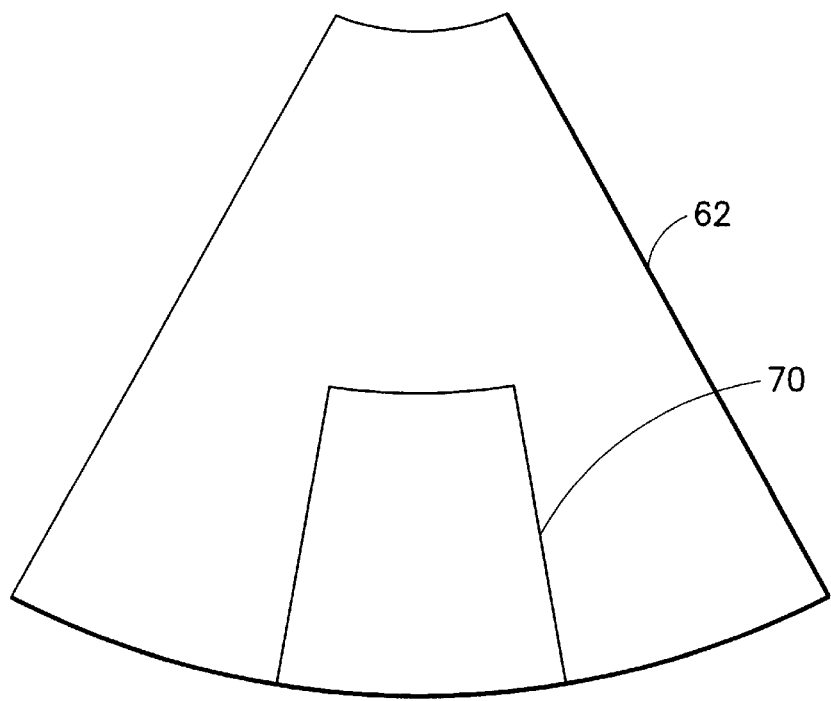
FIG. 7 is a schematic depicting a sector scan in which the ROI image of FIG. 4 has been moved to the bottom of the background image area and adjusted in accordance with the algorithm of the preferred embodiment.
Figure 8:
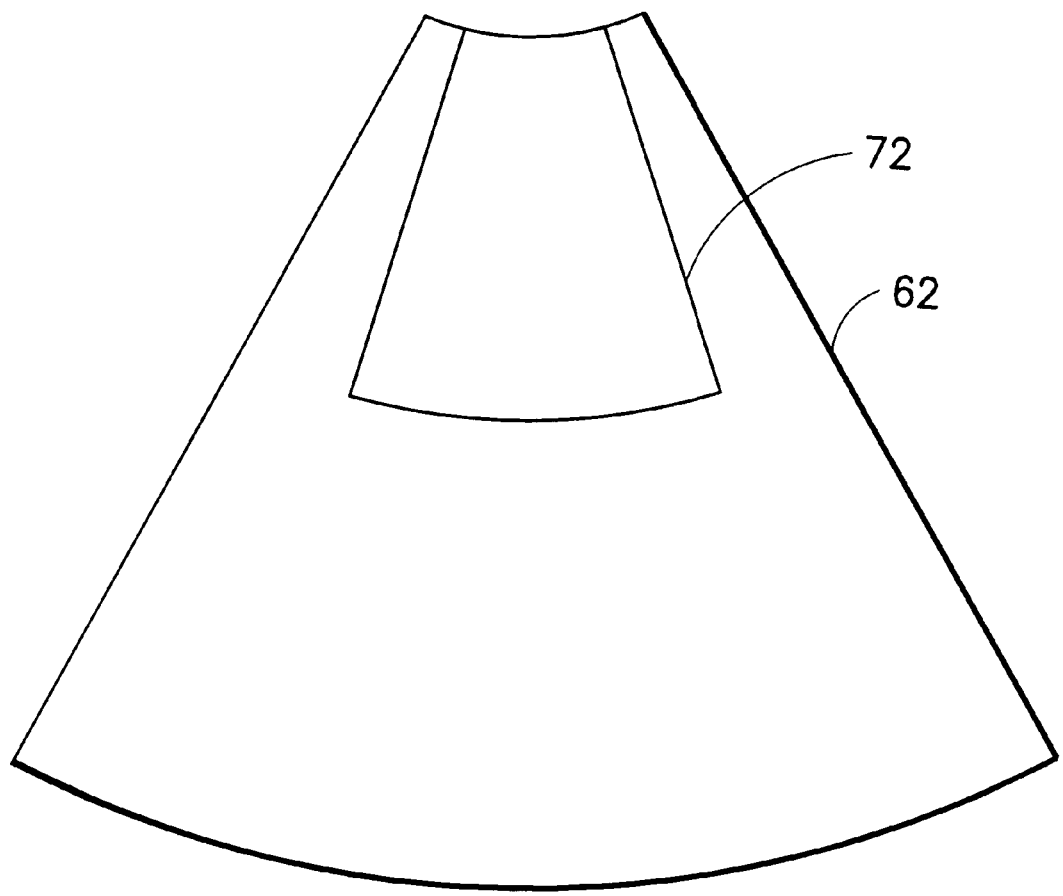
FIG. 8 is a schematic depicting a sector scan in which the ROI image of FIG. 4 has been moved to the top of the background image area and adjusted in accordance with the algorithm of the preferred embodiment.

In contrast to the foregoing conventional algorithm, the algorithm employed in the present invention does not seek to maintain a constant number of vectors in an ROI during position changes. Instead the algorithm in accordance with the preferred embodiment maintains the height and the bottom width of the ROI constant during operator-initiated changes in the ROI position. Only the top width of the ROI is automatically changed in response to the position change. For example if the user moves the ROI deeper in the image (e.g., from the default position shown in FIG. 4 to the position shown in FIG. 7), the height and the width of the bottom of the ROI are not changed, i.e., the height and bottom width of ROI 70 in FIG. 7 will be the same as the height and bottom width respectively of ROI 64 in FIG. 4. The width at the top of the ROI 70, however, is increased and the angles of the edges of the ROI 70 are changed such that the ROI edges are respectively parallel to the leftmost and rightmost vectors of color flow data within the bottom region of ROI 70. If instead, the user moves the ROI shallower in the image, the height of the ROI and the width of the bottom of the ROI are again unchanged. As seen in FIG. 8, the width at the top of the ROI 72 is decreased relative to the top width of ROI 64 in FIG. 4 and the angles of the edges of the ROI 72 are again changed such that the ROI edges are respectively parallel to the leftmost and rightmost vectors of color flow data within the bottom region of ROI 70.

In accordance with one preferred embodiment, the first imaging mode is the B mode and the second imaging mode is the color Doppler mode. In another preferred embodiment, the first imaging mode is the B mode and the second imaging mode is a zoom B mode. In yet another preferred embodiment, the first imaging mode is a non-optimal image quality B mode and the second imaging mode is an optimal image quality B mode.

In each preferred embodiment, the shape of the ROI is automatically adjusted in response to a change in ROI depth. Both the ROI and the image frame on which the ROI is placed are in the shape of a sector of an annular ring, i.e., a top arc and a bottom arc connected at their respective ends by left and right edge lines, the arcs of both the ROI and the image frame having a common center of curvature at which the projections of the edge lines intersect. This common center of curvature is referred to herein as the "apex of the image frame". In accordance with the preferred embodiments, the height and width of the ROI are not changed as the depth of the ROI is changed. The height is the distance from the midpoint of the bottom arc of the ROI to the midpoint of the top arc, while the width is the distance from the midpoint of the bottom arc of the ROI to the point at which the projection of one edge line of the ROI intersects a line tangent to the midpoint of the bottom arc. The host computer or a dedicated graphics processor (not shown) computes the angle included between the midline from the apex of the image frame to the midpoint of the bottom arc and a line projecting from an edge line to the apex of the image frame. Based on that angle, the half-width and the distance of the bottom arc midpoint to the image frame apex, the computer or graphics processor determines the coordinates of those pixels on the display monitor which are to be filled with graphics data representing one edge line of the ROI. A similar computation is done to determine the coordinates of those pixels on the display monitor which are to be filled with graphics data representing the other edge line of the ROI. Also the coordinates of those pixels on the display monitor which are to be filled with graphics data representing the top and bottom arcs of the ROI are determined. The computer or graphics processor then inputs the data representing the ROI graphic into a graphic display memory at the addresses corresponding to the determined pixel coordinates.

In the preferred embodiment in which color flow data is to be superimposed in an ROI on an image frame of B-mode data, after the boundaries of a new ROI have been determined in response to an operator-actuated change in ROI depth, the host computer 44 (see FIG. 1) transmits new beam parameters to the transmit and receive beamformers 28 and 30 for use in the color flow mode. These beam parameters limit the acquisition of color flow data to a region in the scan plane substantially corresponding to the ROI on the image frame. The same principle of operation applies in the other preferred embodiments, to wit, the system computer broadcasts a first set of beam parameters for acquiring data in a region of the scan plane in the first imaging mode and broadcasts a second set of beam parameters for acquiring data in only that portion of the region of the scan plane corresponding to the ROI in the second imaging mode.

Figure 10:
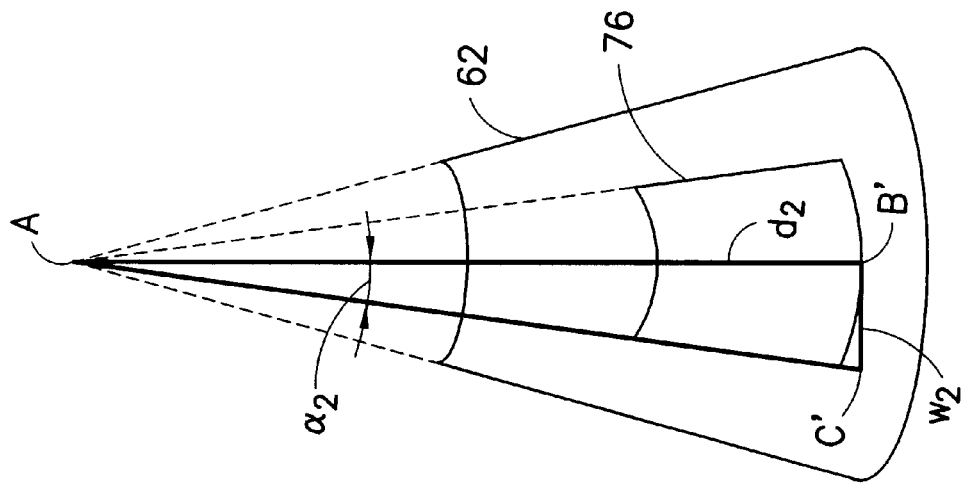
FIGS. 9 and 10 are schematics depicting the geometry used to calculate the respective half-widths of an ROI at initial (FIG. 9) and final (FIG. 10) positions in accordance with the algorithm of the preferred embodiment.
Figure 9:
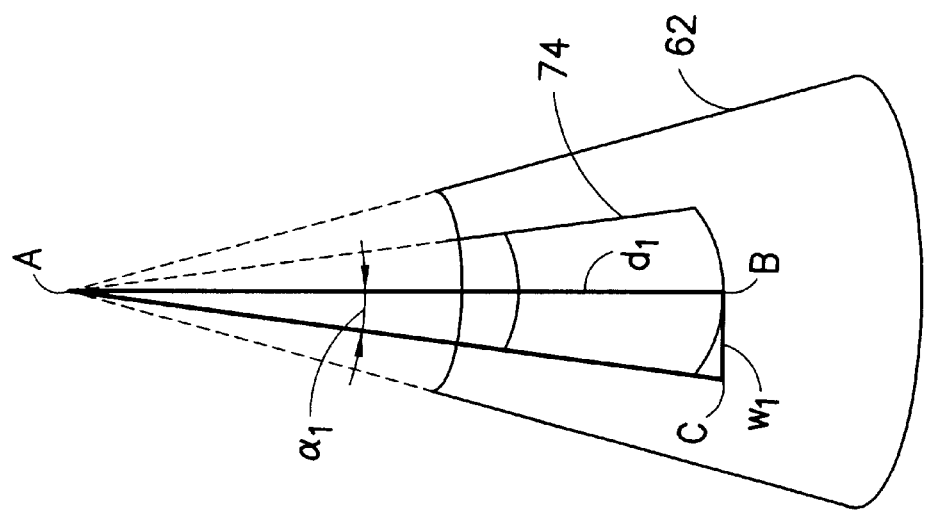

In accordance with the preferred embodiment of the invention, at the start of the algorithm the host computer has stored in its memory two parameters which define the initial location of the ROI. Referring to FIG. 9, the first parameter is the depth $d_1$, which is the distance from the image apex A to the center B of the bottom of ROI 74, and the second parameter is the angle $\alpha_1$, which is the angle between the line segment AB and a line segment AC collinear with the left edge of the ROI 74. The half-width $w_1$ of the ROI 74 (line BC in FIG. 9) can then be computed from $d_1$ and $a_1$ as follows:

$$w_1 = d_1 \tan\alpha_1 \qquad (9)$$

where the angle between line segments AB and BC is a right angle. In accordance with the preferred embodiment, when the user moves the ROI to the position shown in FIG. 10 without changing either the height or the bottom width of the ROI, the host computer first determines the new depth $d_2$, i.e., the movement directly dictates the distance from the image apex A to the center B' of the new ROI 76. The half-width $w_2$ (line segment B'C') of the new ROI 76 is set equal to the half-width $w_1$ of the old ROI 74, where the angle between line segments AB' and B'C' is again a right angle. With both $d_2$ and $w_2$ known, the host computer then calculates the new angle $\alpha_2$ between line segments AB' and AC' as $$\alpha_2 = \tan^{-1}(w_2/d_2) \tag{10}$$

This angle defines the orientation of the left edge of the ROI 76. The same computation can be performed for the other half of the ROI, thereby defining the orientation of the right edge of the ROI 76.

In accordance with the foregoing algorithm, the host computer is also programmed to calculate the pixel coordinates for the midpoint of the bottom arc of the ROI 76 (point B' in FIG. 10) as a function of the positioning of the ROI by the user. The height and the width of the ROI 76 are also already known, i.e., the height and width are the same as for the ROI 74 shown in FIG. 9. Computation of the angle between the left edge and the centerline (line segment AB') of the ROI 76, in combination with the ROI height and width and the pixel coordinates of the bottom midpoint, allows the host computer to compute the pixel coordinates of the left edge of the ROI 76. Similarly, the host computer computes the pixel coordinates of the right edge of the ROI 76. The pixel coordinates of the ROI bottom can be computed based in part on the pixel coordinates of B' and the radius $d_2$ (line segment AB'), while the pixel coordinates of the ROI top can be computed based in part on the pixel coordinates of B' and the radius $(d_2 - h)$, where h is the height of the ROI. The host computer outputs graphics data to addresses in the graphics display memory 41 corresponding to the set of pixel coordinates representing ROI 76. It should be appreciated that the computations of the ROI pixel coordinates are performed instantaneously in response to operator inputs changing the position of the ROI.

In accordance with another preferred embodiment, the first imaging mode is a non-optimal image quality B mode and the second imaging mode is an optimal image quality B mode. In this embodiment, the optimal image quality within the ROI is achieved by using a set of imaging parameters which are different than the set of imaging parameters used to acquire the image data in the background region. The different imaging parameters of the ROI as compared to the background region may include, e.g., different (e.g., shorter) transmit waveforms, an increased number of transmit focal zones per unit depth, different transmit and/or receive apertures, different center frequencies for the receive bandpass filter (primary and/or (sub)harmonics), and higher vector density (i.e., decreased vector spacing). Since the optimal imaging is restricted to an ROI, a high frame rate is still possible within the ROI depending on its size. The background image (outside the ROI) is to be maintained at or above some minimum acceptable level in terms of resolution and/or frame rate.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. For example, the ROI adjustment function is not limited to being implemented in an ultrasound imaging system, but instead can be implemented in any phased array imaging system which uses a curved linear or sector transducer array. In addition, the computations may be performed by a dedicated graphics processor instead of by the host computer. Also, the half-width need not be computed as the distance along the line segment connecting the midpoint of the bottom arc with a projection of an edge line. For example, the half-width could in the alternative be computed as half the distance along a line segment connecting the endpoints of the bottom arc. Regardless of which computation is used, the half-width is maintained constant in response to changes in ROI depth. Therefore, it is intended that the invention not be limited to the particular embodiment disclosed as the best mode contemplated for carrying out this invention, but that the invention will include all embodiments falling within the scope of the appended claims.

What is claimed is:

1. A method for displaying a region of interest graphic, comprising the steps of:

displaying an image frame, said image frame having a reference point;

displaying a region of interest graphic on said image frame at a depth determined relative to said reference point, said region of interest graphic having a bottom width, a top width, a height, and an angle between a projection of a first edge line and a projection of a second edge line;

changing the depth of said region of interest; and changing the top width and the angle of said region of interest graphic as a function of the change in depth, while maintaining the height and the bottom width of said region of interest graphic substantially unchanged.

2. The method as recited in claim 1, wherein the top width is increased in response to an increase in depth and decreased in response to a decrease in depth.

3. The method as recited in claim 1, wherein the angle is increased in response to an increase in depth and decreased in response to a decrease in depth.

4. The method as recited in claim 1, wherein said region of interest graphic comprises first and second arcs connected at their respective ends by said first and second edge lines, said first and second arcs having a common center of curvature at said reference point, and said projections of said edge lines intersecting at said reference point.

5. The method as recited in claim 4, wherein said step of changing the top width and angle of said region of interest graphic comprises the steps of:

determining a half-width of the bottom width; and determining an angle included between said first edge line and a midline connecting said reference point and a midpoint of said second arc as a function of the half-width and the depth.

6. The method as recited in claim 1, further comprising the steps of:

acquiring imaging data in a first imaging mode for display on that portion of said image frame lying within said region of interest graphic; and acquiring imaging data in a second imaging mode for display on at least that portion of said image frame lying outside said region of interest graphic.

7. The method as recited in claim 6, wherein said acquiring step in said first imaging mode comprises the step of interrogating a first region of a scanning plane corresponding to said portion of said image frame lying outside said region of interest graphic with beams of wave energy, and said acquiring step in said second imaging mode comprises the step of interrogating a second region of said scanning plane corresponding to said region of interest with beams of wave energy.

8. The method as recited in claim 6, wherein each of said acquiring steps comprises the steps of transmitting beams of ultrasound energy into a body and detecting ultrasound energy returned from said body following each transmission.

9. The method as recited in claim 1, wherein said step of changing the depth of said region of interest graphic comprises the step of manipulating an input device on an operator interface.

10. An imaging method comprising the steps of:
acquiring first imaging data in a first imaging mode from a first region in a scan plane;
acquiring second imaging data in a second imaging mode from a second region in said scan plane;
displaying said first imaging data in a region of interest of an image frame having a reference point, said region of interest being in the shape of a sector of an annular ring and placed at a depth determined relative to said reference point;
displaying said second imaging data in a portion of said image frame lying outside said region of interest;
changing the depth of said region of interest;
adjusting the shape of said region of interest by changing a top width of said region of interest as a function of the change in depth while maintaining a height and a bottom width of said region of interest substantially constant;
acquiring third imaging data in said first imaging mode from a third region in said scan plane;
acquiring fourth imaging data in said second imaging mode from a fourth region in said scan plane;
displaying said third imaging data in said adjusted region of interest; and
displaying said fourth imaging data in a portion of said image frame lying outside said adjusted region of interest.

11. The method as recited in claim 10, wherein each of said acquiring steps comprises the steps of transmitting beams of ultrasound energy into a body and detecting ultrasound energy returned from said body following each transmission.

12. The method as recited in claim 10, further comprising the step of displaying a region of interest graphic superimposed on said image frame and bounding said adjusted region of interest.

13. The method as recited in claim 12, wherein said region of interest graphic comprises first and second arcs connected at their respective ends by said first and second edge lines, said first and second arcs having a common center of curvature at said reference point, and said projections of said edge lines intersecting at said reference point.

14. The method as recited in claim 10, wherein the top width is increased in response to an increase in depth and decreased in response to a decrease in depth.

15. An imaging system comprising:
a display subsystem;
means for controlling said display subsystem to display an image frame, said image frame having a reference point;
means for controlling said display subsystem to display a region of interest graphic on said image frame at a depth determined relative to said reference point, said region of interest graphic having a bottom width, a top width, a height, and an angle between a projection of a first edge line and a projection of a second edge line;
means for changing the depth of said region of interest; and means for changing the top width and the angle of said region of interest graphic as a function of the change in depth, while maintaining the height and the bottom width of said region of interest graphic substantially unchanged.

16. An imaging system comprising:
a display subsystem;
means for acquiring first imaging data in a first imaging mode from a first region in a scan plane;
means for acquiring second imaging data in a second imaging mode from a second region in said scan plane;
means for controlling said display subsystem to display said first imaging data in a region of interest of an image frame having a reference point, said region of interest being in the shape of a sector of an annular ring and placed at a depth determined relative to said reference point;
means for controlling said display subsystem to display said second imaging data in a portion of said image frame lying outside said region of interest;
means for changing the depth of said region of interest;
means for adjusting the shape of said region of interest by changing a top width of said region of interest as a function of the change in depth, while maintaining a height and a bottom width of said region of interest substantially constant;
means for acquiring third imaging data in said first imaging mode from a third region in said scan plane;
means for acquiring fourth imaging data in said second imaging mode from a fourth region in said scan plane;
means for controlling said display subsystem to display said third imaging data in said adjusted region of interest; and
means for controlling said display subsystem to display said fourth imaging data in a portion of said image frame lying outside said adjusted region of interest.

17. The system as recited in claim 16, wherein said acquiring means comprise an ultrasound transducer array, a transmitter for activating said ultrasound transducer array to transmit beams of ultrasound energy into a body, and a receiver for detecting ultrasound energy returned to said ultrasound transducer array from said body following each transmission.

18. The system as recited in claim 16, further comprising means for controlling said display subsystem to display a region of interest graphic superimposed on said image frame and bounding said adjusted region of interest.

19. The system as recited in claim 16, wherein said region of interest graphic comprises first and second arcs connected at their respective ends by said first and second edge lines, said first and second arcs having a common center of curvature at said reference point, and said projections of said edge lines intersecting at said reference point.

20. The system as recited in claim 16, wherein said means for changing the depth of said region of interest comprise an operator-actuatable input device.

21. An imaging system comprising:
a display subsystem;
a computer operatively coupled to said display subsystem and programmed to perform the following steps:
controlling said display subsystem to display an image frame, said image frame having a reference point;
controlling said display subsystem to display a region of interest graphic on said image frame at a depth determined relative to said reference point, said region of interest graphic having a bottom width, a top width, a height, and an angle between a projection of a first edge line and a projection of a second edge line;

changing the depth of said region of interest; and changing the top width and the angle of said region of interest graphic as a function of the change in depth while maintaining the height and the bottom width of said region of interest graphic substantially unchanged.

22. The system as recited in claim 21, further comprising an array of transducer elements, an array of pulsers respectively coupled to said transducer elements in a transmit mode, and an array of analog-to-digital converters respectively coupled to said transducer elements in a receive mode, wherein said computer is operatively coupled to said pulsers and to said analog-to-digital converters and is further programmed to perform the following steps:

controlling said transducer elements of said array via said pulsers in a first imaging mode to interrogate a first region of a scan plane image frame with beams of wave energy, said background portion lying outside said region of interest;

deriving first imaging mode data from digital data converted by said analog-to-digital converters from wave energy returned to said transducer elements of said array subsequent to each interrogation in said first imaging mode;

controlling said transducer elements of said array via said pursers in a second imaging mode to interrogate a second region of said scan plane corresponding to said region of interest with beams of wave energy;

deriving second imaging mode data from digital data converted by said analog-to-digital converters from wave energy returned to said transducer elements of said array subsequent to each interrogation in said second imaging mode; and controlling said display subsystem to display said first imaging mode data in said background portion of said image frame and to display said second imaging mode data in said region of interest.

23. The system as recited in claim 21, wherein said computer is further programmed to perform the step of controlling said display subsystem to display a region of interest graphic superimposed on said image frame and bounding said region of interest.

24. The system as recited in claim 23, wherein said region of interest graphic comprises first and second arcs connected at their respective ends by said first and second edge lines, said first and second arcs having a common center of curvature at said reference point, and said projections of said edge lines intersecting at said reference point.

25. The system as recited in claim 21, further comprising an operator-actuatable input device connected to said computer, wherein said computer performs said step of changing the depth of said region of interest in response to receipt of a predetermined command input via said input device.

26. The system as recited in claim 22, wherein each of said transducer elements transmits an ultrasound wave in response to an electrical activation signal from a respective pulser and outputs an electrical receive signal to a respective analog-to-digital converter in response to receipt of an ultrasound wave.

27. An imaging system comprising:

an array of transducer elements;

a transmitter programmed to activate said transducer array to transmit a first multiplicity of ultrasound beams focused in a first region in a scan plane in a first imaging mode and a second multiplicity of ultrasound beams focused in a second region in said scan plane in a second imaging mode;

a receiver programmed to form a first set of receive beams of acoustic data from said transducer array subsequent to transmission of said first multiplicity of ultrasound beams in said first imaging mode and a second set of receive beams of acoustic data from said transducer array subsequent to transmission of said second multiplicity of ultrasound beams in said second imaging mode;

a converter for converting said first and second sets of receive beams of acoustic data into first and second sets of pixel intensity data respectively;

a display subsystem;

an input device for selecting a depth of a region of interest of an image frame to be displayed by said display subsystem; and a display controller programmed to perform the following steps:

controlling said display subsystem to display an image frame, said image frame having a reference point;

controlling said display subsystem to display a region of interest graphic on said image frame at a depth determined relative to said reference point, said region of interest graphic having a bottom width, a top width, a height, and an angle between a projection of a first edge line and a projection of a second edge line;

changing the depth of said region of interest in response to a selection of depth input via said input device;

changing the top width and the angle of said region of interest graphic as a function of the change in depth while maintaining the height and the bottom width of said region of interest graphic substantially unchanged; and controlling said display subsystem to display said first set of pixel intensity data in a first region of said image frame lying outside said region of interest graphic and to display said second set of pixel intensity data in a second region of said image frame lying inside said region of interest graphic.

28. An imaging system comprising:

a display subsystem;

an array of transducer elements;

a computer operatively controlling said display subsystem and said array of transducer elements and programmed to perform the following steps:

controlling said array of transducer elements to acquire first imaging data in a first imaging mode from a first region in a scan plane;

controlling said array of transducer elements to acquire second imaging data in a second imaging mode from a second region in said scan plane;

controlling said display subsystem to display said first imaging data in a region of interest of an image frame having a reference point, said region of interest being in the shape of a sector of an annular ring and placed at a depth determined relative to said reference point;

controlling said display subsystem to display said second imaging data in a portion of said image frame lying outside said region of interest;

changing the depth of said region of interest;

adjusting the shape of said region of interest by changing a top width of said region of interest as a function of the change in depth, while maintaining a height and a bottom width of said region of interest substantially constant;

controlling said array of transducer elements to acquire third imaging data in said first imaging mode from a third region in said scan plane;

controlling said array of transducer elements to acquire fourth imaging data in said second imaging mode from a fourth region in said scan plane;

controlling said display subsystem to display said third imaging data in said adjusted region of interest; and controlling said display subsystem to display said fourth imaging data in a portion of said image frame lying outside said adjusted region of interest.

29. The system as recited in claim 28, further comprising an operator-actuatable input device connected to said computer, wherein said computer performs said step of changing the depth of said region of interest in response to receipt of a predetermined command input via said input device.

30. The system as recited in claim 28, wherein each of said transducer elements transmits an ultrasound wave in response to an electrical activation signal from said computer and outputs an electrical receive signal to said computer in response to receipt of an ultrasound wave.

31. A method for changing the position and shape of a region of interest on a display screen, comprising the steps of:

displaying a region of interest having a first shape and a first position on the display screen, said first shape generally conforming to a sector of a first annular ring having a predetermined bottom width, a predetermined top width and a predetermined height;

moving the region of interest from said first position to a second position on the display screen; and displaying the region of interest at said second position in a second shape which generally conforms to a sector of a second annular ring having said predetermined bottom width and said predetermined height, and having a top width different than said predetermined top width.

32. An imaging system comprising:

a display subsystem;

an operator-actuatable input device;

a computer operatively coupled to said display subsystem and to said input device and programmed to perform the following steps:

controlling said display subsystem to display a region of interest having a first shape and a first position, said first shape generally conforming to a sector of a first annular ring having a predetermined bottom width, a predetermined top width and a predetermined height; and controlling said display subsystem to display the region of interest at a second position in a second shape in response to receipt of a predetermined command input via said input device, wherein said second shape generally conforms to a sector of a second annular ring having said predetermined bottom width and said predetermined height, and having a top width different than said predetermined top width.

* * * * *